United States Patent
Dubuffet et al.

(10) Patent No.: US 7,183,308 B1
(45) Date of Patent: Feb. 27, 2007

(54) METOD FOR THE SYNTHESIS OF PERINDOPRIL AND THE PHARMACEUTICALLY ACCEPTABLE SALTS THEREOF

(75) Inventors: Thierry Dubuffet, Autretot (FR); Jean-Pierre Lecouve, Le Havre (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/570,566

(22) PCT Filed: Aug. 27, 2004

(86) PCT No.: PCT/FR2004/002196

§ 371 (c)(1),
(2), (4) Date: Feb. 27, 2006

(87) PCT Pub. No.: WO2005/023841

PCT Pub. Date: Mar. 17, 2005

(30) Foreign Application Priority Data

Aug. 29, 2003 (EP) .................................. 03292131

(51) Int. Cl.
*A61K 31/403* (2006.01)
*C07D 209/12* (2006.01)

(52) U.S. Cl. ...................... 514/412; 548/452
(58) Field of Classification Search ................ 548/452; 514/412
See application file for complete search history.

(56) References Cited

FOREIGN PATENT DOCUMENTS

| EP | 49658 A1 * | 4/1982 |
|---|---|---|
| EP | 1319668 | 6/2003 |
| EP | 1321471 | 6/2003 |
| EP | 1371659 A1 * | 12/2003 |

OTHER PUBLICATIONS

M.A. Huffman, et al., "Improved stereoselectivity in the heterogeneous catalytic synthesis of enalapril obtained through multidimensional screening" Tetrahedron Letters, vol. 40 No. 5 pp. 831-834, Jan. 29, 1999.
T.J. Blacklock, et al., "Synthesis of semisynthetic dipeptides using N-carboxxanhydrides andchiral induction of raney nickel. A method practical for large scale" Journal of Organic Chemistry, vol. 53 No. 4, pp. 836-844, 1988.
International Search Report for PCT/FR2004/002196, Feb. 3, 2005.
European Search Report for EP 03292132, Nov. 18, 2003.

* cited by examiner

*Primary Examiner*—Kamal A. Saeed
*Assistant Examiner*—Michael P. Barker
(74) *Attorney, Agent, or Firm*—Hueschen and Sage

(57) ABSTRACT

A process for the synthesis of perindopril of formula (I):

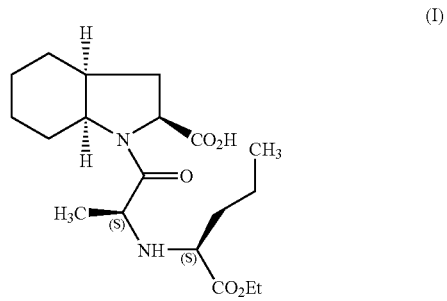

and its pharmaceutically acceptable salts.

9 Claims, No Drawings

METOD FOR THE SYNTHESIS OF PERINDOPRIL AND THE PHARMACEUTICALLY ACCEPTABLE SALTS THEREOF

The present invention relate to a process for the synthesis of perindopril of formula (I):

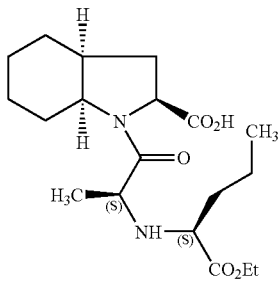

(I)

and its pharmaceutically acceptable salts.

Perindopril and its pharmaceutically acceptable salts, and more especially its tert-butylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in the European patent specification EP 0 049 658.

In view of the pharmaceutical value of this compound, it has been important to be able to obtain it by an effective synthesis process, readily transposable to an industrial scale, that leads to perindopril in a good yield and with excellent purity starting from reasonably priced starting materials.

Patent specification EP 0 308 341 describes the industrial synthesis of perindopril by the coupling of (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation.

The Applicant has now developed a new process for the synthesis of perindopril.

More specifically, the present invention relates to a process for the synthesis of perindopril and its pharmaceutically acceptable salts which is characterised in that the compound of formula (II):

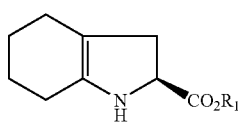

(II)

wherein $R_1$ represents a hydrogen atom or a benzyl or linear or branched ($C_1$–$C_6$)alkyl group, is reacted with a compound of formula (III) having the S configuration:

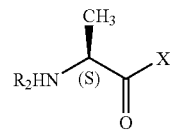

(III)

wherein X represents a halogen atom and $R_2$ represents a protecting group for the amino function, in the presence of a base, to yield, after deprotection of the amino function, a compound of formula (IV):

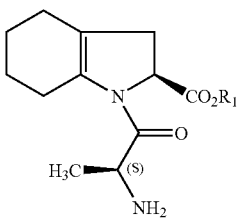

(IV)

wherein $R_1$ is as defined hereinbefore, which is reacted with a compound of formula (V):

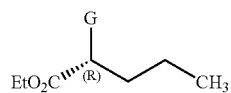

(V)

wherein G represents a chlorine, bromine or iodine atom or a p-toluenesulphonyloxy, methanesulphonyloxy or trifluoromethanesulphonyloxy group, in the presence of a base, to yield a compound of formula (VI):

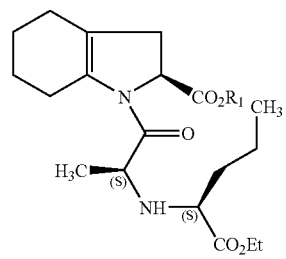

(VI)

wherein $R_1$ is as defined hereinbefore, which is hydrogenated in the presence of a catalyst such as palladium, platinum, rhodium or nickel to yield, after deprotection where necessary, the compound of formula (I).

Among the protecting groups for the amino function that can be used in the process of the present invention, the groups tert-butoxycarbonyl and benzyl may be mentioned without implying any limitation.

R₁ preferably represents a benzyl group. In that case the protecting group for the amino function is preferably the tert-butoxycarbonyl group.

Among the bases that can be used in the reaction between the compounds of formulae (II) and (III) or between the compounds of formulae (IV) and (V) there may be mentioned, without implying any limitation, organic amines such as triethylamine, pyridine, N-methylmorpholine or diisopropylethylamine, and mineral bases such as NaOH, KOH, $Na_2CO_3$, $K_2CO_3$, $NaHCO_3$ or $KHCO_3$.

EXAMPLE 1

(2S,3aS,7aS)-1-{(2S)-2-[(1S)-1-(ethoxycarbonyl)butylamino]-propionyl}-octahydro-1H-indole-2-carboxylic acid tert-butylamine salt Step A: Benzyl (2S)-1-{(2S)-2-[(tert-butoxycarbonyl)amino]propionyl}-2,3,4,5,6,7-hexahydro-1H-indole-2-carboxylate Introduce 200 g of benzyl (2S)-2,3,4,5,6,7-hexahydro-1H-indole-2-carboxylate and 1.5 liters of dichloromethane into a reactor, then bring the temperature of the reaction mixture to 0° C. and add 107 ml of triethylamine and then 162 g of (2S)-2-[(tert-butoxycarbonyl)amino]propionyl chloride. Subsequently, bring the mixture to ambient temperature. After stirring for 1 hour at that temperature, wash the mixture with water and then with a dilute acetic acid solution. The benzyl (2S)-1-{(2S)-2-[(tert-butoxycarbonyl)amino]propionyl}-2,3,4,5,6,7-hexahydro-1H-indole-2-carboxylate solution so obtained is used as it is in the following Step.

Step B: Benzyl (2S)-1-{(2S)-2-aminopropionyl}-2,3,4,5,6,7-hexahydro-1H-indole-2-carboxylate Introduce the solution obtained in the above Step into a reactor, and then add 133 g of trifluoroacetic acid. After stirring for 1 hour 30 minutes at ambient temperature, wash the mixture with water and then with a saturated solution of sodium hydrogen carbonate and evaporate off the solvents to yield benzyl (2S)-1-{(2S)-2-aminopropionyl}-2,3,4,5,6,7-hexahydro-1H-indole-2-carboxylate.

Step C: Benzyl (2S)-1-{(2S)-2-[(1S)-1-(ethoxycarbonyl)butylamino]propionyl}-2,3,4,5,6,7-hexahydro-1H-indole-2-carboxylate Introduce into a reactor 200 g of the compound obtained in the above Step, 106 ml of diisopropylethylamine and 1.5 liters of tetrahydrofuran, and then 183 g of ethyl (2R)-2-p-toluenesulphonyloxy-pentanoate, and subsequently heat at 70° C. for 2 hours. After returning to ambient temperature, the mixture is washed with water and then concentrated to dryness. The residue is taken up in dichloromethane. A hydrochloric acid solution (2M) is added until a pH of about 7.5 is obtained. After decanting, the solvents are evaporated off to yield benzyl (2S)-1-{(2S)-2-[(1S)-1-(ethoxycarbonyl)butylamino]propionyl}-2,3,4,5,6,7-hexahydro-1H-indole-2-carboxylate.

Step D: (2S,3aS,7aS)-1-{(2S)-2-[(1S)-1-(ethoxycarbonyl)butylamino]propionyl}-octahydro-1H-indole-2-carboxylic acid Introduce 200 g of the compound obtained in the above Step, in solution in acetic acid, and then 5 g of 10% Pt/C into a hydrogenation vessel. Hydrogenate under a pressure of 5 bars at from 15 to 30° C. until the theoretical amount of hydrogen has been absorbed. Remove the catalyst by filtration and then cool to from 0 to 5° C. and collect the solid obtained by filtration. Wash the cake and dry it to constant weight.

The (2S,3aS,7aS)-1-{(2S)-2-[(1S)-1-(ethoxycarbonyl)butylamino]propionyl}octahydro-1H-indole-2-carboxylic acid is thereby obtained in a yield of 85% and with an enantiomeric purity of 98%.

Step E: (2S,3aS,7aS)-1-{(2S)-2-[1S)-1-(ethoxycarbonyl)butylamino]propionyl}-octahydro-1H-indole-2-carboxylic acid tert-butylamine salt The precipitate obtained in the above Step (200 g) is dissolved in 2.8 liters of acetonitrile, and then 40 g of tert-butylamine and 0.4 liters of ethyl acetate are added.

The suspension obtained is then refluxed until dissolution is complete, and the solution obtained is subsequently filtered hot and cooled, with stirring, to a temperature of from 15 to 20° C. The resulting precipitate is then filtered off, made into a paste again with acetonitrile, dried and then recrystallised from ethyl acetate to give the expected product in a yield of 95% and with an enantiomeric purity of 99%.

EXAMPLE 2

(2S,3aS,7aS)-1-{(2S)-2-[(1S)-1-(ethoxycarbonyl)butylamino]-propionyl}-octahydro-1H-indole-2-carboxylic acid tert-butylamine salt Steps A and B: identical to Steps A and B of Example 1.

Step C Benzyl (2S)-1-{(2S)-2-[(1S)-1-(ethoxycarbonyl)butylamino]propionyl}-2,3,4,5,6,7-hexahydro-1H-indole-2-carboxylate Introduce 200 g of the compound obtained in the above Step, 106 ml of diisopropylethylamine and 1.5 liters of ethyl acetate into a reactor, followed by 165 g of ethyl (2R)-2-chloropentanoate, and then heat at 50° C. for 3 hours. After returning to ambient temperature, the mixture is washed with water and then concentrated to dryness. The residue is taken up in dichloromethane. A hydrochloric acid solution (2M) is added until a pH of about 7.5 is obtained. After decanting, the solvents are evaporated off to yield benzyl (2S)-1-{(2S)-2-[(1S)-1-(ethoxycarbonyl)butylamino]propionyl}-2,3,4,5,6,7-hexahydro-1H-indole-2-carboxylate.

Steps D and E: identical to Steps D and E of Example 1.

The invention claimed is:

1. A process for the synthesis of compounds of formula (I):

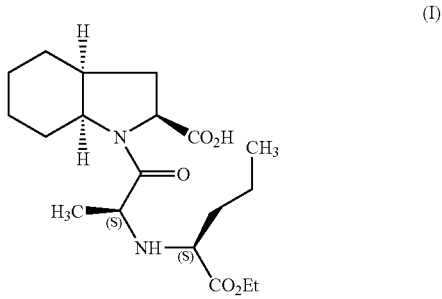

and pharmaceutically acceptable salts thereof,
wherein a compound of formula (II):

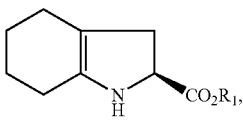
(II)

wherein $R_1$ represents a hydrogen atom, a benzyl group or a linear or branched $(C_1-C_6)$alkyl group,
is reacted with a compound of formula (III) having the S configuration:

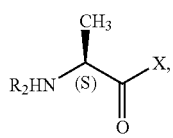
(III)

wherein X represents a halogen atom and $R_2$ represents a protecting group for the amino function,
in the presence of a base,
to yield, after deprotection of the amino function, a compound of formula (IV):

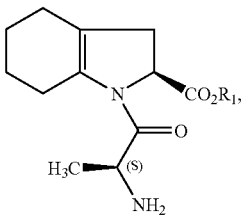
(IV)

which is reacted with a compound of formula (V):

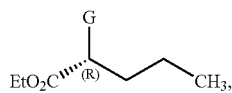
(V)

wherein G represents a chlorine, bromine or iodine atom or a p-toluenesulphonyloxy, methanesulphonyloxy or trifluoromethanesulphonyloxy group,
in the presence of a base,
to yield a compound of formula (VI):

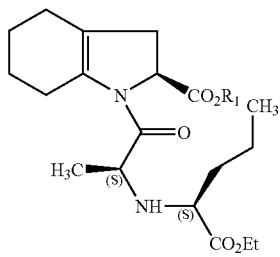
(VI)

which is hydrogenated in the presence of a catalyst
to yield, after deprotection where necessary, the compound of formula (I).

2. The process of claim 1, wherein the protecting group for the amino function is a tert-butoxycarbonyl or benzyl group.

3. The process of claim 2, wherein $R_1$ represents a benzyl group, and the protecting group for the amino function is a tert-butoxycarbonyl group.

4. The process of claim 1, wherein the base used for the reaction between the compounds of formula (II) and (III) is an organic amine selected from triethylamine, pyridine, N-methylmorpholine and diisopropylethylamine, or a mineral base.

5. The process of claim 4, wherein the mineral base is selected from NaOH, KOH, $Na_2CO_3$, $K_2CO_3$, $NaHCO_3$, and $KHCO_3$.

6. The process of claim 1, wherein the base used for the reaction between the compounds of formulae (IV) and (V) is an organic amine selected from triethylamine, pyridine, N-methylmorpholine and diisopropylethylamine, or a mineral base.

7. The process of claim 6, wherein the mineral base is selected from NaOH, KOH, $Na_2CO_3$, $K_2CO_3$, $NaHCO_3$, and $KHCO_3$.

8. The process of claim 1, wherein the hydrogenation catalyst is selected from palladium, platinum, rhodium and nickel.

9. The process of claim 1 for the synthesis of perindopril in the form of its tert-butylamine salt.

* * * * *